(12) United States Patent
Malmqvist et al.

(10) Patent No.: US 6,503,760 B2
(45) Date of Patent: Jan. 7, 2003

(54) METHOD FOR CAPTURING ANALYTES ELUTED FROM SURFACE-BOUND LIGANDS

(75) Inventors: Magnus Malmqvist, Uppsala (SE); Östen Jansson, Storvreta (SE)

(73) Assignee: Biacore AB, Uppsala (SE)

( * ) Notice: Subject to any disclaimer, the term of this patent is extended or adjusted under 35 U.S.C. 154(b) by 0 days.

(21) Appl. No.: 09/810,937

(22) Filed: Mar. 16, 2001

(65) Prior Publication Data

US 2002/0012929 A1 Jan. 31, 2002

Related U.S. Application Data

(60) Provisional application No. 60/190,336, filed on Mar. 16, 2000.

(51) Int. Cl.$^7$ ............................................ G01N 33/543
(52) U.S. Cl. ...................... 436/518; 436/524; 436/528; 435/7.1; 435/7.92; 210/656; 210/691; 210/511; 530/413; 422/82.11
(58) Field of Search ................................ 435/7.1, 7.92; 436/518, 532, 536, 538, 524, 528; 210/656, 659, 691, 755, 768, 203, 511, 198.2; 422/82.11; 530/413

(56) References Cited

U.S. PATENT DOCUMENTS

| | | | | |
|---|---|---|---|---|
| 5,236,826 A | * | 8/1993 | Marshall et al. | 435/7.92 |
| 5,236,849 A | * | 8/1993 | Ishikawa et al. | 436/540 |
| 5,312,730 A | * | 5/1994 | Piran et al. | 435/7.92 |
| 5,395,587 A | * | 3/1995 | Brigham-Burke et al. | 422/68.1 |
| 5,756,717 A | * | 5/1998 | Paliwal et al. | 536/123.1 |
| 5,888,834 A | * | 3/1999 | Ishikawa et al. | 436/518 |
| 5,955,729 A | * | 9/1999 | Nelson et al. | 250/282 |
| 5,989,806 A | * | 11/1999 | Brust et al. | 435/5 |
| 5,989,926 A | * | 11/1999 | Badley et al. | 436/538 |
| 6,025,197 A | * | 2/2000 | Sheppard et al. | 435/325 |
| 6,127,129 A | * | 10/2000 | Corn et al. | 435/6 |
| 6,159,426 A | * | 12/2000 | Palmer et al. | 422/68.1 |
| 6,289,286 B1 | * | 9/2001 | Andersson et al. | 702/19 |
| 6,294,391 B1 | * | 9/2001 | Badley et al. | 436/518 |

FOREIGN PATENT DOCUMENTS

| | | | |
|---|---|---|---|
| GB | WO 97/44664 | * | 11/1997 |
| WO | WO 94/00213 | | 1/1994 |
| WO | WO 94/07912 | | 4/1994 |

* cited by examiner

*Primary Examiner*—Christopher L. Chin
*Assistant Examiner*—Gary Counts
(74) *Attorney, Agent, or Firm*—Seed IP Law Group PLLC

(57) ABSTRACT

Methods for capturing analytes associated with surface-bound ligands are disclosed. The methods involve eluting analytes from surface-bound ligands with a first liquid to generate free analytes, and capturing the free analytes with a solid capturing material within the first liquid to generate a first liquid containing captured analytes. The first liquid may be a flowing liquid or a non-flowing liquid, and the surface to which the surface-bound ligand is attached may be a sensing surface, such as a biosensor, or a non-sensing surface. The captured analytes may be further consolidated at a location removed from the surface-bound ligand, eluted from the solid capturing material with a second liquid, and used for subsequent analysis or procedures.

19 Claims, No Drawings

METHOD FOR CAPTURING ANALYTES ELUTED FROM SURFACE-BOUND LIGANDS

CROSS-REFERENCE TO RELATED APPLICATION

This application claims the benefit of U.S. Provisional Patent Application No. 60/190,336 filed Mar. 16, 2000, which provisional application is incorporated herein by reference in its entirety.

TECHNICAL FIELD

This invention relates generally to methods for capturing analytes associated with surface-bound ligands and, more specifically, to use of a solid capturing material for capturing analytes eluted from surface-bound ligands.

BACKGROUND OF THE INVENTION

A variety of analytical techniques are used to characterize interactions between molecules, particularly in the context of assays directed to the detection of biomolecular interactions. For example, antibody:antigen interactions are of fundamental importance in many fields, including biology, immunology and pharmacology. In this context, many analytical techniques involve binding of a "ligand" (such as an antibody) to a solid support, followed by contacting the ligand with an "analyte" (such as an antigen). Following contact of the ligand and analyte, some characteristic is measured which is indicative of the interaction, such as the ability of the ligand to bind the analyte. After measurement of the interaction, the ligand:analyte pair is typically disrupted with an elution and/or regeneration solution in order to regenerate surface-bound ligand for further analytical measurement.

The freed analyte of the ligand:analyte pair, however, is commonly not reused; rather, the freed analyte is typically disposed of together with the elution and/or regeneration solution. This practice is undesirable because researchers very often have only limited quantities of the analyte for analytical measurement purposes, and because researchers very often desire to perform further analytical measurements directed to the analyte itself. Accordingly, there is a need in the art to effectively consolidate freed analyte from a ligand:analyte pair such that the freed analyte is amenable to subsequent analytical measurement.

The need to effectively consolidate freed analyte for subsequent analytical measurement may be illustrated in the context of biosensors which use surface plasmon resonance (SPR) to monitor the interactions between an analyte and a ligand bound to a solid support. In this regard, a representative class of biosensor instrumentation is sold by Biacore AB (Uppsala, Sweden) under the trade name BIAcore® (hereinafter referred to as "the BIAcore instrument"). The BIAcore instrument includes a light emitting diode, a sensor chip covered with a thin gold film, an integrated microfluidic cartridge and photo detector. Incoming light from the diode is reflected in the gold film and detected by the photo detector. At a certain angle of incidence ("the SPR angle"), a surface plasmon resonance wave is set up in the gold layer, which is detected as an intensity loss or "dip" in the reflected light. The theoretical basis behind the BIAcore instrument has been fully described in the literature (see, e.g., Jönsson, U. et al., *Biotechniques* 11:620–627 (1991)).

In addition to SPR analysis using the BIAcore instrument, researchers are beginning to appreciate the synergistic effects of coupling SPR technology with other analytical techniques. In this context, the real-time interaction analysis offered by the BIAcore instrument complements other known methods for investigating both biomolecular structure and function. For example, SPR has recently been coupled with mass spectroscopy (i.e., SPR-MS) to provide an extremely powerful micropreparative technique for biomolecular investigations (see, e.g, PCT International Publication No. WO 97/09608). In connection with SPR-MS, analyte is freed from the surface-bound ligand by matrix-assisted laser desorption/ionization for subsequent analytical measurement by mass spectrometry.

One of the problems posed by eluting analyte away from surface-bound ligands for subsequent analytical measurements is that substantial amounts of analyte can be lost due to nonspecific binding of analyte to the walls and other components of the microfluidic cartridge as the elution and/or regeneration solution flows through the microfluidic cartridge. Moreover, once eluted away from surface-bound ligands, analyte must still be consolidated so that there will be enough sample for subsequent analysis. Accordingly, there is a need in the art for improved methods and micropreparative techniques for consolidating biomolecules associated with surface-bound ligands. The present invention fulfills these needs, and provides further related advantages.

SUMMARY OF THE INVENTION

In brief, the present invention is directed to methods for capturing an analyte associated with a surface-bound ligand, as well as to methods for consolidating the same. In one embodiment, the method involves eluting the analyte from the surface-bound ligand by contacting the surface-bound ligand with a first liquid flow that dissociates the analyte from the surface-bound ligand to generate a free analyte within the first liquid flow. The free analyte is then captured by a solid capturing material that is carried within the first liquid flow, yielding a first liquid flow containing captured analyte. The surface to which the surface-bound ligand is attached may be either a sensing surface, such as a sensing surface of a biosensor, or a non-sensing surface.

In an alternative embodiment, the method involves eluting the analyte from the surface-bound ligand on a surface of a biosensor by contacting the surface-bound ligand with a first liquid that dissociates the analyte from the surface-bound ligand to generate a free analyte within the first liquid. The free analyte is then captured by a solid capturing material that is within the first liquid, yielding a first liquid containing captured analyte. In this embodiment, the surface to which the surface-bound ligand is attached is a surface of a biosensor, and the first liquid may be a flowing or non-flowing liquid.

In both of the above embodiments, the captured analyte may be further consolidated with similarly captured analytes at a location removed from the surface-bound ligand. Such consolidation may, for example, be accomplished by passing the captured analytes of the first liquid through a separation device that prevents passage of the captured analytes, but allows passage of the first liquid. Once consolidated, the captured analytes may be contacted with a second liquid that elutes the analyte of the captured analyte from the solid capturing material to yield free analyte, which may then be used in subsequent analytical techniques or procedures.

These and other aspects of the present invention will be evident upon reference to the following detailed description. To this end, various references are cited throughout this application to further illustrate specific aspects of this invention. Such documents are each incorporated herein by reference in their entirety.

DETAILED DESCRIPTION OF THE INVENTION

As mentioned above, the present invention is directed to methods for capturing an analyte associated with surface-bound ligand with a solid capturing material. In a first embodiment, the solid capturing material is carried within a first liquid flow and the surface to which the surface-bound ligand is attached is a sensing or non-sensing surface. In a second embodiment, the solid capturing material is within a first liquid (flowing or non-flowing) and the surface to which the surface-bound ligand is attached is the surface of a biosensor.

In the first embodiment, a method is disclosed for capturing an analyte associated with a surface-bound ligand by eluting the analyte from the surface-bound ligand by contacting the surface-bound ligand with a first liquid flow that dissociates the analyte to generate a free analyte within the first liquid flow. For example, a surface that has been utilized for capturing a solubilized biomolecule (e.g., "real-time" monitoring of analyte-ligand biomolecular interactions with a biosensor) will have an analyte associated with its surface-bound ligand. The analyte is typically associated (e.g., bound) to the ligand by non-covalent forces (such as electrostatic and Lewis acid-Lewis base forces). In the context of this invention, the agent bound to the surface is referred to as a "surface-bound ligand", while the agent that associates with the surface-bound ligand is referred to as an "analyte."

To this end, the terms "ligand" and "analyte" are to be construed broadly, and encompass a wide variety of molecules ranging from small molecules to large proteins, as well as a variety of interaction pairs. For example, representative analyte:ligand interaction pairs include, but are not limited to, the following (wherein the analyte is listed first, followed by the ligand with which the analyte is associated, the names of the analyte and ligand being separated by a colon): antigen:antigen-specific antibody, antigen-specific antibody:antigen, hormone: hormone receptor, hormone receptor:hormone, polynucleotide:complementary polynucleotide, avidin/streptavidin:biotin, biotin:avidin/streptavidin, enzyme:enzyme substrate or inhibitor, enzyme substrate or inhibitor:enzyme, lectins:specific carboxyhydrate, specific carboxyhydrate:lectins, lipids:lipid binding proteins or membrane-associated proteins, lipid binding proteins or membrane-associated proteins:lipids, polynucleotides:polynucleotide binding proteins, polynucleotide binding proteins:polynucleotides, receptor:transmitter, transmitter:receptor, drug:target, target:drug, as well as more general types of interactions such as protein:protein, protein:polynucleotide, polynucleotide:protein, DNA:DNA, DNA:RNA, and RNA:DNA interactions. Moreover, it is to be understood that the analyte may come from a single source, a mixture of natural compounds, a gene library, a mRNA or protein displayed gene library, or a chemical library of any kind.

Thus, in accordance with the practice of this invention, the analyte is eluted from the surface-bound ligand by contacting the same with a first liquid flow that dissociates the analyte from the surface-bound ligand. Such elution or dissociation of the analyte from the surface-bound ligand may be accomplished by use of any number of suitable elution liquids or regeneration solutions (referred to herein as the "first liquid" and as the "second liquid"). For example, aqueous solutions comprising at least one acidic, basic, ionic, organic, detergent or chelating agent may be utilized as the first and second liquid. Such aqueous solutions include those described in the journal article entitled *Identification and Optimization of Regeneration Conditions for Affinity-Based Biosensor Assays* (Andersson, K et al., *Anal. Chem.* 71(13):2475–81 (Jul. 1, 1999)), which article is incorporated herein by reference in its entirety.

More generally, and has been reported in the literature, various classes of analyte:ligand systems may be disrupted under the following exemplary conditions: (1) Antibody:antigen interaction pairs—to varying degrees with hydrochloric acid (HCl) of different concentrations (Malmborg et al, *Scandinavial Journal of Immunology* 35:643–50, 1992; Ward et al., *Biochemistry International* 26:559–65, 1992) or with weaker acids, typically phosphoric or formic (Corr et al., *Journal of Experimental Medicine* 178:1877–92, 1993; VanCott et al., *Journal of Immunological Methods* 183:103–17, 1995), or with detergent or chaotropic solutions (Tanchou et al., *AIDS Research and Human Retroviruses*, 10:983–93 1994; End et al., *Journal of Biological Chemistry* 268:10066–75, 1993); (2) Receptor:transmitter interaction pairs—with acids (Morelock et al., *Journal of Medicinal Chemistry* 38:1309–18, 1995), bases (Lemmon et al., *Journal of Biological Chemistry* 269:31653–58, 1994), under chaotropic conditions and high ion strength (Stitt et al., *Cell* 80:661–70, 1995), or under natural dissociation conditions (Ma et al., *Journal of Biological Chemistry* 39:24430–36, 1994); (3) DNA interaction pairs—under very mild regeneration conditions using detergents, EDTA, or under natural dissociation conditions (Cheskis et al., *Molecular Endocrinology* 1996; Casasnovas *Journal of Biological Chemistry* 270:13216–24, 1995); and (4) Glycoprotein interaction pairs—under acid conditions or using sugar solutions (Okazaki et al., *Journal of Molecular Recognition* 8:95–99 1995). The precise conditions for eluting the analyte from the surface-bound ligand will, of course, depend upon the system under investigation. However, such conditions may readily be determined by those having skill in the art.

In the first embodiment of the present invention, the first liquid is in flowing contact with surface-bound ligand (referred to herein as the "first liquid flow"). Suitable devices for contacting the first liquid flow with the surface-bound analyte are known in the art, and are generally referred to as fluidic delivery systems. A representative fluidic delivery system is the integrated microfluidic cartridge utilized in the BIAcore instrument discussed previously in the Background section, and which is capable of precisely and controllably flowing a liquid over a surface. Such delivery systems are known in the art, such as described by U.S. Pat. Nos. 5,313,264 and 5,443,890 (both of which are incorporated herein by reference).

Carried within the first liquid flow is a solid capturing material which is capable of capturing the free analyte eluted from the surface-bound ligand. In other words, the solid capturing material is allowed to flow together with the first liquid within the fluidic flow channel(s) that bring the first liquid flow into contact with the surface-bound ligand. In this manner, the solid capturing material captures, typically by adsorption or absorption, the analyte in close proximity to the surface-bound ligand from which it is eluted, thereby reducing the amount of free analyte lost due to nonspecific binding, such as binding of free analyte to the walls and other components of the fluidic channel(s). Because of the small size typically associated with fluidic flow channels, exemplary solid capturing material typically constitutes separation beads of a small diameter (e.g., 2 to 10 micrometers). Further, the solid capturing material is generally selected to be suitable with the analyte:ligand system under investigation—that is, the material should be of a type that will readily capture the eluted analyte. In this regard, there are a wide variety of solid capture materials that meet these parameters.

As mentioned above, exemplary solid capturing materials are separation beads, such as chromatographic beads used in liquid column adsorption chromatography, especially chromatographic beads used in high performance liquid chromatography (HPLC). However, the present invention is not limited to chromatographic beads. Rather, any solid capturing material adapted to the separation of solute in a solution on the basis of physicochemical properties may be employed. Accordingly, the solid capturing materials of the present invention are inclusive of all chromatographic media, as well as other solid or semi-solid supports having similar properties (such as polymer-based particulate solid supports). Therefore, the term "solid capturing material," as used within the context of the present invention, is to be construed broadly and is inclusive of essentially any solid or semi-solid support made of a synthetic, semi-synthetic and/or naturally occurring organic polymer, wherein such polymer(s) has the ability to adsorb analytes that have been freed from surface bound ligands; it also encompasses various inorganic materials having like properties. Preferably, however, the solid capturing materials of the present invention are spherical in shape, comprise a silica gel material having an amorphous structure, and are somewhat porous. The solid capturing material may also be magnetic in nature, such as magnetic beads (especially useful for subsequent elution via ionization as in MALDI). Moreover, the solid capturing materials of the present invention may be derivatized with a wide range of chemical functionalities, as is appreciated by those skilled in the art, for specifically adsorbing the freed analyte of interest. Exemplary in this regard are bead materials made from agarose, dextran, hydroxyapatit, silica, polyacrylamid, and hydrophilic polymers in cross-linked form, which bead materials may also be porous, nonporous, and/or dense.

Thus, in one aspect of the present invention, the solid capturing material are separation beads carried within the first liquid flow. In one embodiment, a plurality of separation beads carried within the first liquid flow are pumped through the one or more flow cells of a biosensor, such as the flow cells of the BIAcore instrument. Preferably, the flow rate is such that the first liquid flow is larninar. As is appreciated by those skilled in the art, a laminar flow rate will tend to centrally concentrate the separation beads carried within the flow liquid stream (i.e., the beads will generally tend to flow in the center of the channel). This phenomenon (also known as hydrodynamic focusing) is due to the shear forces exerted by the wall of conduit onto the flowing liquid. The shear forces will cause a flow rate gradient across the flow channel; a flowing bead will tend to flow centrally so as to have the same or symmetrical flow forces on both of its sides.

In the first embodiment of this invention, the surface to which the surface-bound ligand is attached may be either a sensing surface or a non-sensing surface. Thus, a sensing surface in accordance with the present invention may be a sensing surface of a biosensor; such a sensing surface comprises a solid metal support (e.g., gold or silver) having a coating of a densely packed organic monolayer thereon (as is disclosed in U.S. Pat. No. 5,436,161, which is incorporated herein by reference in its entirety.) The sensing surface may further comprise a biocompatible porous matrix like, for example, a hydrogel (e.g., a polysaccharide such as dextran) coupled to the organic monolayer coating so to be operable in association with a biosensor.

As is appreciated by those skilled in the art, a biosensor is an analytical device for analyzing minute quantities of sample solution having an analyte of interest, wherein the analyte is analyzed by a detection device that may employ any one of a variety of detection methods. Typically, such methods include, but are not limited to, mass detection methods, such as piezoelectric, optical, thermo-optical and surface acoustic wave (SAW) device methods, and electrochemical methods, such as potentiometric, conductometric, amperometric and capacitance methods. With regard to optical detection methods, representative methods include those that detect mass surface concentration, such as reflection-optical methods, including both internal and external reflection methods, angle, wavelength or phase resolved, for example ellipsometry and evanescent wave spectroscopy (EWS), the latter including surface plasmon resonance (SPR) spectroscopy, Brewster angle refractometry, critical angle refractometry, frustrated total reflection (FTR), evanescent wave ellipsometry, scattered total internal reflection (STIR), optical wave guide sensors, evanescent wave-based imaging, such as critical angle resolved imaging, Brewster angle resolved imaging, SPR angle resolved imaging, and the like. Further, photometric methods based on, for example, evanescent fluorescence (TIRF) and phosphorescence may also be employed, as well as waveguide interferometers. While certain aspects of the present invention are hereinafter illustrated in the context of the BIAcore instrument (Biacore AB, Uppsala, Sweden) with its SPR-based technology, it is to be understood that the present invention is not limited to such systems.

In a second embodiment of this invention, a method is disclosed for capturing an analyte associated with a surface-bound ligand on a surface of a biosensor by eluting the analyte from the surface-bound ligand to generate a free analyte within a first liquid, and capturing the free analyte with a solid capturing material within the first liquid to generate a first liquid containing captured analyte. This embodiment is practiced in the same manner as disclosed above, except that the first liquid may be either a flowing or non-flowing liquid when in contact with the surface-bound ligand. To the extent that the first liquid is a flowing liquid, this embodiment represents a specific aspect of the first embodiment wherein the surface to which the surface-bound ligand is attached is a biosensor surface, and is fully described above. In contrast, when the first liquid is a non-flowing liquid, the first liquid may be contacted with the surface-bound ligand by any number of procedures and/or devices, including, for example, stop-flow fluidic liquid delivery techniques, as well as simple aspiration of the first liquid onto (and off of) the surface-bound ligand of the biosensor. In this embodiment, the solid capturing material is within the first liquid at the point of capturing the free analyte, but need not have been carried within the first liquid. Rather, the solid capturing material may, for example, be added to the first liquid after the step of eluting.

Accordingly, in this aspect of the invention, it should be understood that the term "biosensor" covers not only analytical devices that use flow systems to contact the first liquid with the surface-bound ligand, such as the integrated microfluidic cartridge of the BIAcore instrument, but also includes analytical devices that use non-flow systems to contact the first liquid with a sensing surface, such as a sensing surface on the bottom of a cuvette. As such, this aspect of the present invention is applicable to both flow and non-flow biosensor systems.

In both the first and second embodiments of this invention, and following capture of the free analyte by the solid capture material to generate the first liquid containing captured analyte and more typically a plurality of captured analytes, the captured analytes are consolidated at a location remote from the surface-bound ligand. Such consolidation may, for example, be accomplished by utilizing a column (such as a column used in micropreparative HPLC) that traps the solid capturing material (e.g., the separation beads), but allows passage of the first liquid. For example, in the embodiment wherein the first liquid is in flowing contact with the surface-bound ligand, a column may be operatively connected to an exit portal so as to receive the flowing first liquid following contact with the surface-bound ligand. The column may be sieved in a manner so as to trap the solid separation beads—but allow passage of the first liquid. In this manner, the separation beads having captured analyte will consolidate within the column, whereas the first liquid will be discharged.

The consolidation step, however, is not limited to columns; rather, any technique that at least partially separates the solid capturing material from the first liquid may be employed in the practice of the present invention. Exemplary in this regard is any other device capable of aggregating the solid capturing material, such as decanting devices that allow the solid capturing material to settle, centrifuge devices that allow the first liquid to be separated from the solid capturing material, and filtering devices that prevent passage of the solid capturing materials but allow passage of the first liquid, and devices for attracting magnetic beads.

In still another aspect, and following consolidation within the column or other consolidation device, the captured analyte may be contacted with a second liquid so as to elute the bound analyte. Thus, and in one embodiment, a second liquid is allowed to pass through the column having the plurality of captured analytes therein to thereby free the analyte. Because the solid capturing material is consolidated within the column, the freed analyte in the second eluent is typically of such concentration so as to be useful for a further analytical measurement, such as mass-spectroscopy, as well as for other uses (e.g., other analytical techniques or procedures). As with selection of the first liquid, the selection of the second liquid depends upon the system under investigation (i.e., depends upon the nature of the coupling force between the analyte and the solid capturing material). As discussed above in the context of disrupting analyte-:ligand pairs, proper elution conditions for various analyte-solid capturing material combinations may readily be determined by those having skill in the art.

In still yet another aspect, and following consolidation within the column or other consolidation device, the captured analyte may be subjected to matrix-assisted laser desorption/ionization time-of-flight mass spectrometry. In this embodiment, the solid capturing material may have an outer surface that comprises an appropriate matrix (e.g., nicotonic or sinapinic acid). In general, an analyte captured on or in such a matrix is amenable to intact desorption by laser irradiation as is appreciated by those skilled in the art.

The following examples are offered by way of illustration, and not restriction.

EXAMPLES

Example 1

Biosensor instrument: BIACORE® 3000 (Biacore AB, Uppsala, Sweden)
Sensor chip: CM 5 (Biacore AB, Uppsala, Sweden)
Coupling reagent: Amine Coupling Kit (Biacore AB, Uppsala, Sweden)
Capturing molecule: HIV protease Q7K 981126 (provided by Uppsala University; Dr. Helena Danielsson)
Analyte: HIV inhibitor Saquvinavir (provided by Medivir AB, Sweden)
Capturing media: RP 2 Porous 10 micrometer diameter reversed phase media (PerSeptive Biosystems, CA, U.S.A.)
Elution liquid: 2% Formic acid (prepared from 98–100% formic acid; PA Riedel de Haen, Germany)
Mass spectrometer: Bruker Biflex III™ (Bruker Daltonics Inc., U.S.A.)

The capturing molecule is immobilized to the sensor chip using the instrument supplier's standard protocol for amine coupling resulting in ca 4000 RU per flowcell relative to the baseline in a serial injections of flowcells 4, 3, 2 in BIACORE 3000. Analyte is then injected, the immobilized amount of HIV protease being able to capture 30–100 RU of HIV inhibitor—corresponding to 50–150 femtomole inhibitor per flowcell.

The captured analyte is recovered by using 4 µl slurry of a 2–4% slurry of chromatographic beads in 2% formic acid which is injected using the "MICRORECOVER" command in BIACORE 3000. The beads are equilibrated in a gelloader tip according to Gobom et al., *J. Mass. Spectrom.* 34:105–116, 1999, and then dispensed in about 50 µl 2% formic acid prior to MICRORECOVER. Recovered beads with the captured analyte are then transferred manually with an Eppendorff pipette on top of a gelloader tip with already equilibrated RPC gel according to Gobom et al., supra. A washing step involving elution with 5% acetonitrile (ACN) in 0.1% trifluoroacetic acid (TFA) is then performed, and the analyte is subsequently eluted with 45% ACN/0.1% TFA saturated with α-cyanocinnamic acid directly onto a MALDI probe tip according to Gobom et al., supra. The presence of recovered analyte is then verified by MALDI MS performed on the Bruker BiflexIII mass spectrometer in reflectron mode.

Example 2

The procedure described in Example 1 above is followed, except that as capturing media are used Micromer®-M C8, C18 reversed phase, 8 µm diameter magnetic beads (Micromod Partikeltechnologie GmbH, Rostock, Germany). Prior to injection into the BIACORE 3000 by the MICRORECOVER command, the chromatographic magnetic beads are equilibrated in 2% formic acid by filtration using a batch procedure. A 2–4% slurry of the equlibrated beads are then prepared in 2% formic acid and transferred to an autosampler vial for injection into the BIACORE 3000.

While the present invention has been described in the context of the embodiments illustrated and described herein, the invention may be embodied in other specific ways or in other specific forms without departing from its spirit or essential characteristics. Therefore, the described embodiments are to be considered in all respects as illustrative and not restrictive. The scope of the invention is, therefore, indicated by the appended claims rather than by the foregoing description, and all changes that come within the meaning and range of equivalency of the claims are to be embraced within their scope.

What is claimed is:

1. A method for capturing an analyte, comprising the sequential steps of:
   contacting the analyte with a biosensor surface, the surface having a ligand bound thereto, so as to form an an analyte:surface-bound ligand interaction pair;
   detecting the binding of the analyte to the surface-bound ligand;

eluting the analyte from the surface-bound ligand by contacting the biosensor surface with a first liquid that dissociates the analyte from the surface-bound ligand to generate a free analyte within the fist liquid;

capturing the free analyte with a particulate solid capturing material within the first liquid, to thereby generate a first liquid containing captured analyte;

removing the particulate solid capturing material, having the captured analyte associated therewith, to a location remote from the biosensor surface and consolidating the particulate solid capturing material, having the captured analyte associated therewith, at said location; and freeing the analyte from the particulate solid capturing material.

2. The method of claim 1 wherein the analyte:surface-bound ligand interaction pair is selected from the group consisting of antigen:antigen-specific antibody, antigen-specific antibody:antigen, hormone:hormone receptor, hormone receptor:hormone, polynucleotide:complementary polynucleotide, avidin/streptavidin:biotin, biotin:avidin/streptavidin, enzyme:enzyme substrate, enzyme:enzyme inhibitor, enzyme substrate:enzyme, enzyme inhibitor:enzyme, lectins:carboxyhydrate, carboxyhydrate:lectins, lipid:lipid binding protein, lipid:membrane-associated protein, lipid binding protein:lipid, membrane-associated protein:lipids, polynucleotide:polynucleotide binding protein, polynucleotide binding protein:polynucleotide, receptor:transmitter, transmitter:receptor, drug:target, target:drug, protein:protein, protein:polynucleotide, polynucleotide:protein, DNA:DNA, DNA:RNA, and RNA:DNA.

3. The method of claim 2 wherein the analyte:surface-bound ligand interaction pair is an antigen:antibody interaction pair.

4. The method of claim 1 wherein the biosensor is an affinity-based biosensor.

5. The method of claim 4 wherein the affinity-based biosensor is a surface plasmon resonance biosensor.

6. The method of claim 1 wherein the first liquid is an aqueous solution comprising at least one acidic, basic, ionic, organic, detergent or chelating agent.

7. The method of claim 1 wherein the particulate solid capturing material is separation beads.

8. The method of claim 7 wherein the separation beads are made from agarose, dextran, hydroxyapatit, silica, polyacrylamid, or hydrophilic polymers.

9. The method of claim 8 wherein the separation beads comprise chromatographic media having spherical shapes with diameters ranging from 2 to 10 micrometers.

10. The method of claim 7 wherein the separation beads have magnetic properties.

11. The method of claim 1 wherein the analyte:surface-bound ligand interaction pair is a plurality of analyte:surface-bound ligand interaction pairs, the step of eluting the analyte from the surface-bound ligand generates a plurality of free analytes, the step of capturing generates a plurality of captured analytes, the consolidated, particulate solid capturing material has a plurality of captured analytes associated therewith, and a plurality of analytes are freed from the particulate solid capturing material.

12. The method of claim 11 wherein the step of consolidating comprises passing the particulate solid capturing material, having the plurality of captured analytes associated therewith and carried within the first liquid, through a separation device that prevents passage of the particulate solid capturing materials having the plurality of captured analytes associated therewith, while allowing passage of the first liquid, and, thereby, consolidating the plurality of captured analytes.

13. The method of claim 12 wherein the separation device comprises a column, and the first liquid containing the plurality of captured analytes is passed through the column.

14. The method of claim 11, wherein the step of freeing the plurality of analytes from the particulate solid capturing material is accomplished by eluting the plurality of captured analytes from the particulate solid capturing material by contacting the consolidated and captured plurality of analytes with a second liquid that dissociates the plurality of captured analytes from the particulate solid capturing material to yield a second liquid comprising a plurality of free analytes.

15. The method of claim 14 wherein the second liquid is an aqueous solution comprising at least one acidic, basic, ionic, organic, detergent or chelating agent.

16. The method of claim 14 wherein eluting the plurality of free analytes from the particulate solid capturing material occurs in a column employed to consolidate the particulate solid capturing material having the plurality of captured analytes associated therewith.

17. The method of claim 14 wherein the second liquid comprising the plurality of free analytes is collected, and the plurality of free analytes are subjected to subsequent analysis.

18. The method of claim 1 wherein the removal of the particulate solid capturing material to the location remote from the biosensor surface is accomplished by flowingly carrying the solid capturing material, while within the first liquid, away from the biosensor surface, then further transporting the solid capturing material to the remote location.

19. The method of claim 1 further comprising the step of subjecting the freed analyte to a subsequent analysis.

* * * * *

UNITED STATES PATENT AND TRADEMARK OFFICE
CERTIFICATE OF CORRECTION

PATENT NO.      : 6,503,760 B2
DATED           : January 7, 2003
INVENTOR(S)     : Magnus Malmqvist et al.

It is certified that error appears in the above-identified patent and that said Letters Patent is hereby corrected as shown below:

<u>Column 9,</u>
Line 4, "analyte within the fist liquid" should read -- analyte within the first liquid --.

Signed and Sealed this

Seventeenth Day of June, 2003

JAMES E. ROGAN
*Director of the United States Patent and Trademark Office*